US006277090B1

(12) United States Patent
Crawford, Jr.

(10) Patent No.: US 6,277,090 B1
(45) Date of Patent: Aug. 21, 2001

(54) NOSE CLEANING SYSTEM

(76) Inventor: Raymond Crawford, Jr., 27 Vernon Rd., Everett, WA (US) 98205

( * ) Notice: Subject to any disclaimer, the term of this patent is extended or adjusted under 35 U.S.C. 154(b) by 0 days.

(21) Appl. No.: 09/195,825

(22) Filed: Nov. 19, 1998

(51) Int. Cl.$^7$ ............... A61M 35/00; A47K 7/02
(52) U.S. Cl. ............... 604/1; 15/176.2; 15/209.1; 15/244.4
(58) Field of Search ............... 604/1–3; 15/176.1, 15/176.2, 209.1, 210.1, 244.1, 244.4

(56) References Cited

U.S. PATENT DOCUMENTS

| | | | |
|---|---|---|---|
| 2,362,704 | * | 11/1944 | McGivern ............... 604/1 |
| 3,586,380 | * | 6/1971 | Albeckoff ............... 604/1 |
| 4,283,809 | * | 8/1981 | Prost ............... 604/1 |
| 5,120,301 | * | 6/1992 | Wu ............... 604/3 |
| 5,762,494 | * | 6/1998 | Archambault ............... 604/1 |
| 5,766,143 | * | 6/1998 | Bennett ............... 604/1 |
| 5,928,176 | * | 7/1999 | Nakatani ............... 604/1 |
| 5,947,986 | * | 9/1999 | Lewis ............... 604/3 |

* cited by examiner

Primary Examiner—Dennis Ruhl

(57) ABSTRACT

A nose cleaning system is provided including a handle and a nose tip including an ellipsoid mounted with respect to an end of the handle. The nose tip has a foam outer layer defining an outer surface with a hemispherical inboard extent and a tapering outboard extent which terminates in an arcuate apex.

10 Claims, 3 Drawing Sheets

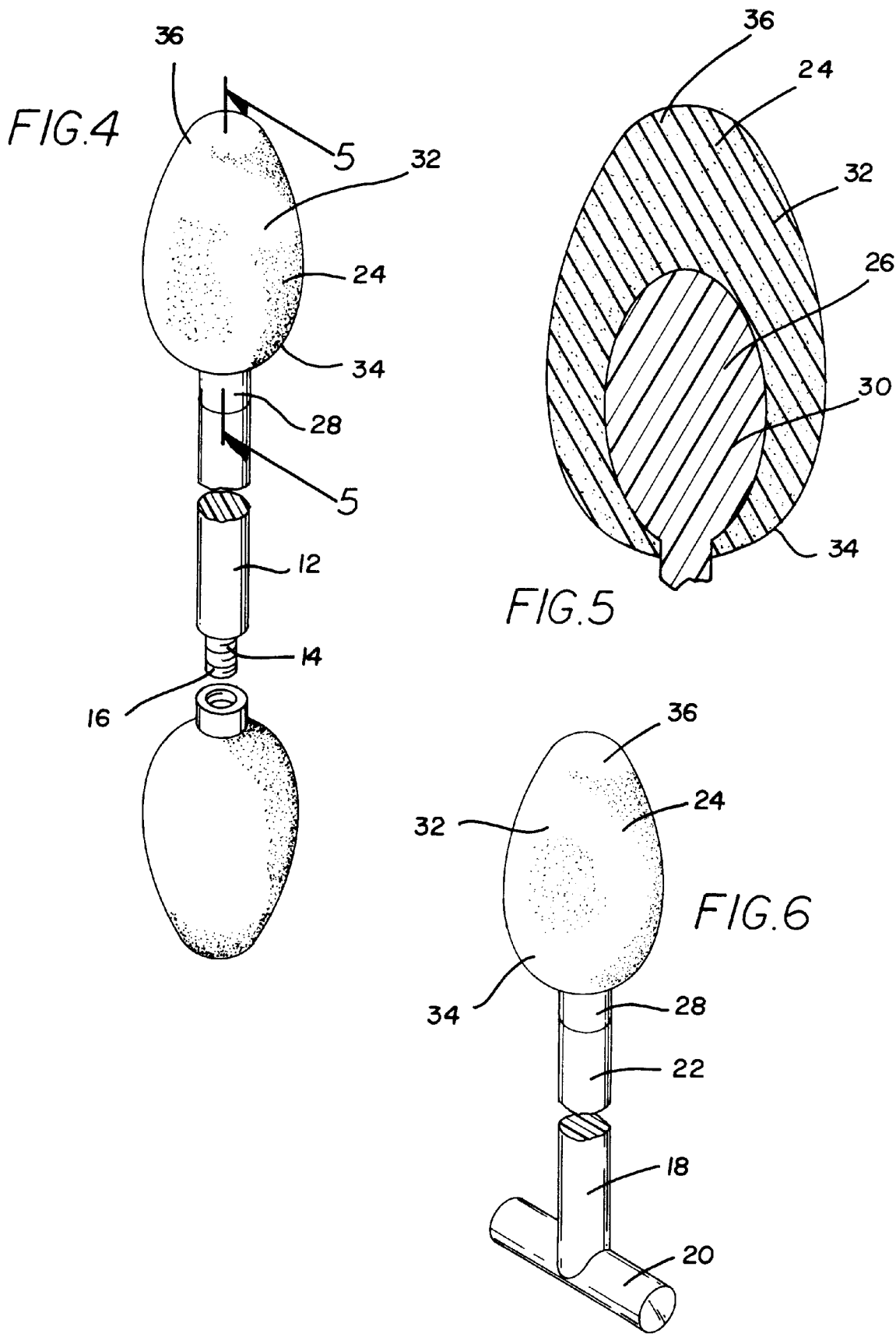

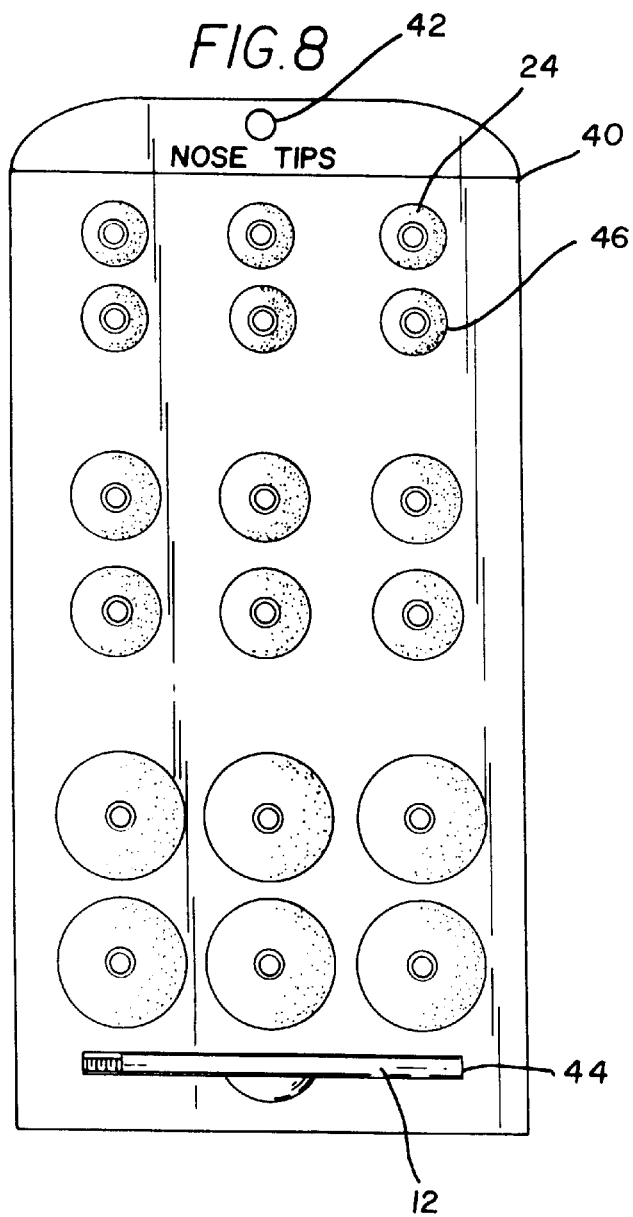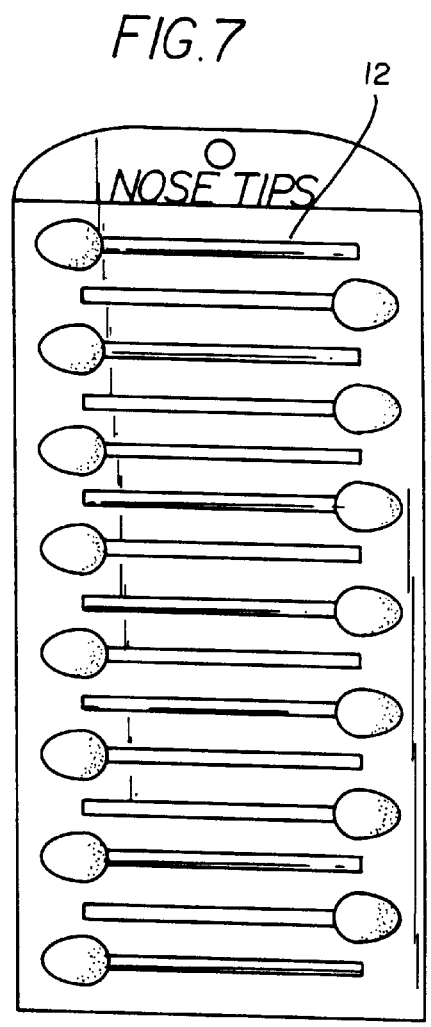

NOSE CLEANING SYSTEM

BACKGROUND OF THE INVENTION

1. Field of the Invention

The present invention relates to swabs and more particularly pertains to a new nose cleaning system for removing dust and debris from a nasal orifice of a user.

2. Description of the Prior Art

The use of swabs is known in the prior art. More specifically, swabs heretofore devised and utilized are known to consist basically of familiar, expected and obvious structural configurations, notwithstanding the myriad of designs encompassed by the crowded prior art which have been developed for the fulfillment of countless objectives and requirements.

Known prior art swabs include U.S. Pat. No. 4,935,001; U.S. Pat. No. 5,531,671; U.S. Pat. No. 3,443,562; U.S. Pat. No. 4,934,011; U.S. Pat. No. 3,508,547; and U.S. Pat. No. Des. 332,658.

In these respects, the nose cleaning system according to the present invention substantially departs from the conventional concepts and designs of the prior art, and in so doing provides an apparatus primarily developed for the purpose of removing dust and debris from a nasal orifice of a user.

SUMMARY OF THE INVENTION

In view of the foregoing disadvantages inherent in the known types of swabs now present in the prior art, the present invention provides a new nose cleaning system construction wherein the same can be utilized for removing dust and debris from a nasal orifice of a user.

The general purpose of the present invention, which will be described subsequently in greater detail, is to provide a new nose cleaning system apparatus and method which has many of the advantages of the swabs mentioned heretofore and many novel features that result in a new nose cleaning system which is not anticipated, rendered obvious, suggested, or even implied by any of the prior art swabs, either alone or in any combination thereof.

To attain this, the present invention generally comprises at least one resilient plastic linear handle having a linear cylindrical configuration. The linear handle is equipped with a pair of coaxial ends each having a reduced diameter and a plurality of external threads formed therein for reasons that will soon become apparent. FIG. 6 shows an optional resilient plastic T-shaped handle having a linear gripping portion and a linear intermediate portion having a length and a diameter greater than that of the gripping portion. The intermediate portion of the T-shaped handle has a first end integrally coupled to a central extent of the gripping portion and extends therefrom in perpendicular relationship therewith. The intermediate portion is further equipped with a coaxial second end having a reduced diameter and a plurality of external threads formed therein. FIGS. 4–6 show a plurality of detachable deformable nose tips each having a resilient plastic base including a cylindrical sleeve. The cylindrical sleeve has an interior space with a plurality of internal threads formed therein and an opening for allowing threaded engagement of the sleeve with the external threads of one of the handles. As shown in FIG. 5, an ellipsoid is mounted on an end of the sleeve opposite the opening such that foci of the ellipsoid reside along an axis of the sleeve. Each deformable nose tip further has a foam outer layer defining an outer surface with a hemispherical inboard extent and a tapering generally frusto-conical outboard extent which terminates in an arcuate apex. Ideally, the foam outer layer is at least twice as thick along the outboard extent thereof with respect to the inboard extent thereof. Associated therewith is a plurality of resilient nose tips each including a cylindrical sleeve having an interior space with a plurality of internal threads similar to the previous deformable nose tips. In contrast, the resilient nose tips are equipped with a planar elliptical portion mounted on an end of the sleeve opposite the opening such that foci of the elliptical portion reside along an axis of the sleeve. FIG. 8 shows a package with a rectangular configuration having a top edge, a bottom edge and a pair of side edges. The package includes a hanging aperture formed in a central extent of the top edge thereof. Further, a linear recess is formed in the package adjacent to the bottom edge thereof for releasably receiving the linear handle. The linear recess has a semispherical recess formed adjacent a central extent thereof for facilitating the removal of the linear handle. The package further includes a plurality of spaced pairs of rows of generally circular recesses formed therein between the top edge and the linear recess. Each pair of rows has recesses of a unique size corresponding to the sizes of the nose tips for removably receiving the same therein.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new nose cleaning system apparatus and method which has many of the advantages of the swabs mentioned heretofore and many novel features that result in a new nose cleaning system which is not anticipated, rendered obvious, suggested, or even implied by any of the prior art swabs, either alone or in any combination thereof.

It is another object of the present invention to provide a new nose cleaning system which may be easily and efficiently manufactured and marketed.

It is a further object of the present invention to provide a new nose cleaning system which is of a durable and reliable construction.

An even further object of the present invention is to provide a new nose cleaning system which is susceptible of a low cost of manufacture with regard to both materials and labor, and which accordingly is then susceptible of low prices of sale to the consuming public, thereby making such nose cleaning system economically available to the buying public.

Still yet another object of the present invention is to provide a new nose cleaning system which provides in the apparatuses and methods of the prior art some of the advantages thereof, while simultaneously overcoming some of the disadvantages normally associated therewith.

Still another object of the present invention is to provide a new nose cleaning system for removing dust and debris from a nasal orifice of a user.

Even still another object of the present invention is to provide a new nose cleaning system that includes a handle and a nose tip including an ellipsoid mounted with respect to an end of the handle. The nose tip has a foam outer layer defining an outer surface with a hemispherical inboard extent and a tapering outboard extent which terminates in an arcuate apex.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 4 is a perspective view of the present invention with the deformable nose tips.

FIG. 5 is a cross-sectional view of the present invention taken along line 5—5 shown in FIG. 4 depicting one of the deformable nose tips.

FIG. 6 is a perspective view of the present invention employing the T-shaped handle.

FIG. 7 is a front view of the package of one of the embodiments of the present invention.

FIG. 8 is a front view of the package of another one of the embodiments of the present invention.

DESCRIPTION OF THE PREFERRED EMBODIMENT

Figure 1:
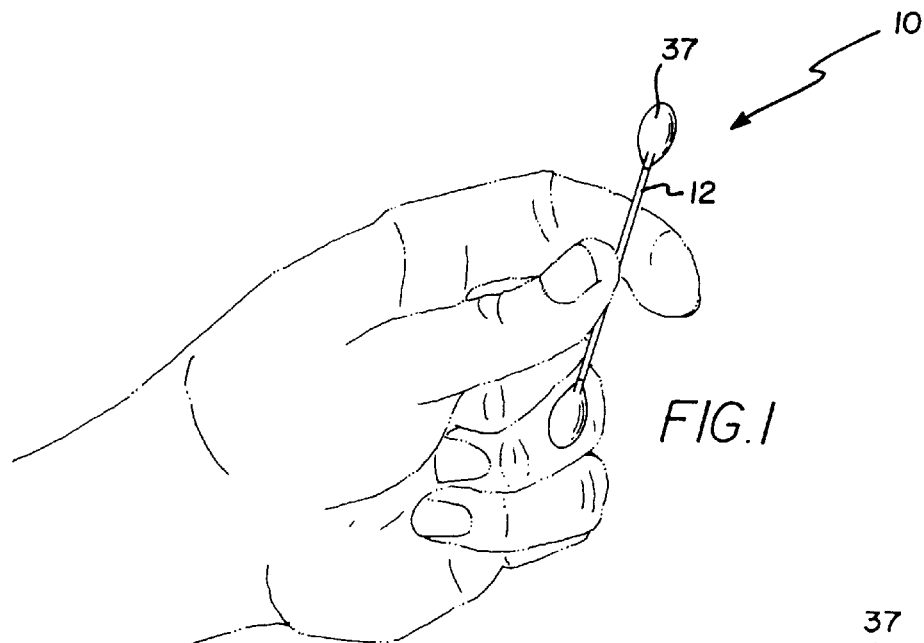
FIG. 1 is a perspective view of a new nose cleaning system according to the present invention.
Figure 2:
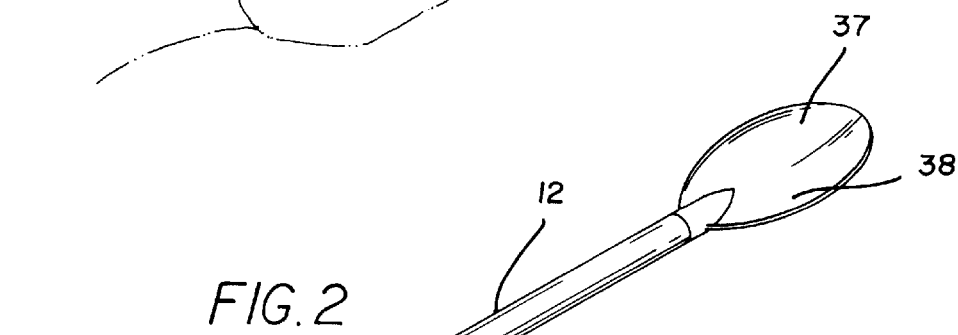
FIG. 2 is a perspective view of the present invention with the resilient nose tips.
Figure 3:
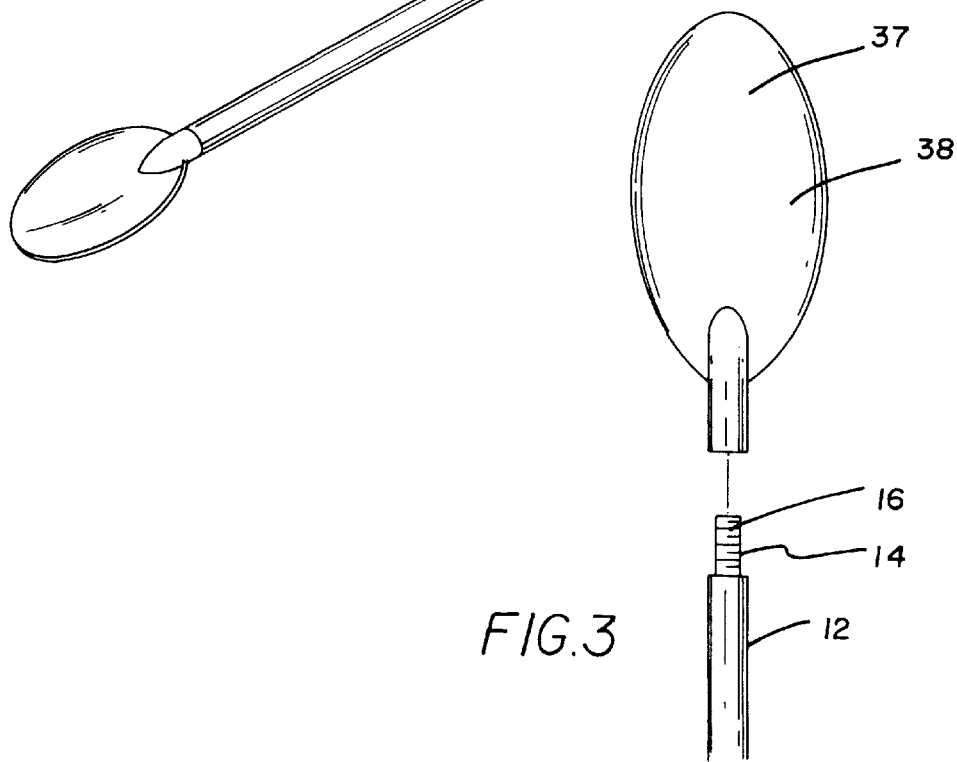
FIG. 3 is a front exploded view of the present invention with the resilient nose tip.

With reference now to the drawings, and in particular to FIGS. 1 through 8 thereof, a new nose cleaning system embodying the principles and concepts of the present invention and generally designated by the reference numeral 10 will be described.

The present invention, designated as numeral 10, includes at least one resilient plastic linear handle 12 having a linear cylindrical configuration. The linear handle is equipped with a pair of coaxial ends 14 each having a reduced diameter and a plurality of external threads 16 formed therein for reasons that will soon become apparent. In another embodiment, only one of the ends may be threaded and the free end may taper outwardly. In the preferred embodiment, the linear handles have a length of about 3–3 and ½ inches and a diameter of about ¼ of an inch.

FIG. 6 shows an optional resilient plastic T-shaped handle 18 having a linear gripping portion 20 and a linear intermediate portion 22 having a length and a diameter greater than that of the gripping portion. Ideally, the length of the intermediate portion is at least four times that of the gripping portion. The intermediate portion of the T-shaped handle has a first end integrally coupled to a central extent of the gripping portion and extends therefrom in perpendicular relationship therewith. The intermediate portion is further equipped with a coaxial second end having a reduced diameter and a plurality of external threads formed therein.

FIGS. 4–6 show a plurality of detachable deformable nose tips 24 each having a resilient plastic base 26 including a cylindrical sleeve 28. The cylindrical sleeve has an interior space with a plurality of internal threads formed therein and an opening for allowing threaded engagement of the sleeve with the external threads of one of the handles. As an option, the plastic base of the nose tips may be integrally coupled to the associated handle. As shown in FIG. 5, an ellipsoid 30 is mounted on an end of the sleeve opposite the opening such that foci of the ellipsoid reside along an axis of the sleeve.

Each deformable nose tip further has a foam outer layer 32 defining an outer surface with a hemispherical inboard extent 34 and a tapering generally frusto-conical, or egg-shaped, outboard extent 36 which terminates in an arcuate apex. Ideally, the foam outer layer is at least twice as thick along the outboard extent thereof with respect to the inboard extent thereof. As shown in FIG. 5, a length of the ellipsoid of the base of the deformable nose tips is about ½ that of the entire nose tip while a width of the ellipsoid of the base is slightly greater than ½ that of the entire nose tip.

Associated therewith is a plurality of resilient nose tips 37 each including a cylindrical sleeve having an interior space with a plurality of internal threads similar to the previous deformable nose tips. Also, it should be noted that the plastic base of the resilient nose tips may be integrally coupled to the associated handle. In contrast to the deformable nose tips, the resilient nose tips are equipped with a planar elliptical portion 38 mounted on an end of the sleeve opposite the opening such that foci of the elliptical portion reside along an axis of the sleeve. It should be noted that the nose tips may be constructed in multiple sizes.

FIG. 8 shows a package 40 with a rectangular configuration having a top edge, a bottom edge and a pair of side edges. The package includes a hanging aperture 42 formed in a central extent of the top edge thereof. Further, a linear recess 44 is formed in the package adjacent to the bottom edge thereof for releasably receiving at least one the linear handle. The linear recess has a semispherical recess formed adjacent a central extent thereof for facilitating the removal of the linear handle. The package further includes a plurality of spaced pairs of rows of generally circular recesses 46 formed therein between the top edge and the linear recess. Each pair of rows has recesses of a unique size corresponding to the sizes of the nose tips for removably receiving the same therein. It should be noted that the recesses of the package may be altered to accommodate the embodiment of the present invention wherein the nose cleaning system are integrally coupled to the handle. Note FIG. 9.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A nose cleaning system comprising:
    a handle;
    a plurality of nose tips, each of said nose tips including an ellipsoid, said ellipsoid being removably mountable to a first end of the handle, each nose tip having a foam outer layer defining an outer surface with a hemispherical inboard extent and a tapering outboard extent which terminates in an arcuate apex;
    wherein the nose tips are detachable with the respect to the handle, wherein the nose tips are detachable from the handle by way of threads; and
    wherein the first end and a second end of the handle have threaded ends for removably coupling with the nose tips.

2. A nose cleaning system as set forth in claim 1, wherein the foam outer layer is at least twice as thick along the outboard extent thereof with respect to the inboard extent thereof.

3. A nose cleaning system as set forth in claim 1, wherein a plurality of the nose tips are included and further included is a package with a plurality of recesses for housing the nose tips and the handle.

4. A nose cleaning system as set forth in claim 1, wherein the handle has a T-shaped configuration.

5. A nose cleaning system as set forth in claim 1, wherein the handle is integrally coupleable to each one of the plurality of nose tips.

6. A nose cleaning system comprising:
    a handle;
    a plurality of nose tips, each of said nose tips including an ellipsoid, said ellipsoid being removably mountable on a first end of the handle, each nose tip having a foam outer layer defining an outer surface with a hemispherical inboard extent and a tapering outboard extent which terminates in an arcuate apex; and
    wherein the handle has a T-shaped configuration.

7. A nose cleaning system as set forth in claim 6 wherein the foam outer layer is at least twice as thick along the outboard extent thereof with respect to the inboard extent thereof.

8. A nose cleaning system as set forth in claim 6 wherein a plurality of the nose tips are included and further included is a package with a plurality of recesses for housing the nose tips and the handle.

9. A nose cleaning system as set forth in claim 6 wherein the handle is integrally coupled to the nose tip.

10. A nose cleaning system comprising, in combination:
    at least one resilient plastic linear handle having a linear cylindrical configuration with a pair or coaxial ends each having a reduced diameter and a plurality of external threads formed therein;
    at least one resilient plastic T-shaped handle having a linear gripping portion and a linear intermediate portion having a length and a diameter greater than that of the gripping portion, the intermediate portion of the T-shaped handle having a first end integrally coupled to a central extent of the gripping portion and extending therefrom in perpendicular relationship therewith and a coaxial second end having a reduced diameter and a plurality of external threads formed therein;
    a plurality of first and second nose tips;
    the first nose tips comprising detachable deformable nose tips each having a resilient plastic base including a cylindrical sleeve having an interior space with a plurality of internal threads formed therein and an opening formed therein for allowing threaded engagement of the sleeve with the external threads of one of the handles and an ellipsoid mounted on an end of the sleeve opposite the opening such that foci of the ellipsoid reside along an axis of the sleeve, each first deformable nose tip having a foam outer layer defining an outer surface with a hemispherical inboard extent and a tapering generally frustoconical outboard extent which terminates in an arcuate apex, wherein the foam outer layer is at least twice as thick along the outboard extent thereof with respect to the inboard extent thereof;
    the second nose tips comprising nose tips each including a cylindrical sleeve having an interior space with a plurality of internal threads formed therein and an opening formed therein for allowing threaded engagement of the sleeve with the external threads of one of the handles and a elliptical portion mounted on an end of the sleeve opposite the opening such that foci of the elliptical portion reside along an axis of the sleeve;
    a package with a rectangular configuration having a top edge, a bottom edge and a pair of side edges, the package including a hanging aperture formed in a central extent of the top edge thereof and a linear recess formed therein adjacent to the bottom edge thereof for releasably receiving the linear handle, the linear recess having a semispherical recess formed adjacent a central extent thereof for facilitating the removal of the linear handle, the package further including a plurality of spaced pairs of rows of generally circular recesses formed therein between the top edge and the linear recess, each pair of rows having recesses of a unique size corresponding to the sizes of the first and second nose tips for removably receiving the same therein.

\* \* \* \* \*